United States Patent [19]

Yerman

[11] Patent Number: 4,860,958

[45] Date of Patent: Aug. 29, 1989

[54] PLASTIC SYRINGE DESTRUCTION DEVICE

[76] Inventor: Emil A. Yerman, 2348 Terrace Ave., South Plainfield, N.J. 07080

[21] Appl. No.: 199,627

[22] Filed: May 27, 1988

[51] Int. Cl.⁴ .......................................... B02C 19/14
[52] U.S. Cl. ......................................... 241/23; 100/38; 100/39; 100/93 P; 100/98 R; 241/65; 241/99; 241/199.11; 264/37; 264/322; 264/DIG. 69
[58] Field of Search ............... 100/38, 39, 93 P, 98 R, 100/269 R; 264/37, 322, DIG. 69; 241/285 R, 99, 199.9, 65, 199.11, 23, 66, 67, 17, 62, 41

[56] References Cited

U.S. PATENT DOCUMENTS

| | | |
|---|---|---|
| 2,731,208 | 1/1956 | Dodd .................................... 241/41 |
| 3,547,577 | 11/1968 | Lovercheck . |
| 3,589,276 | 6/1971 | Swallert ............................ 241/99 X |
| 3,685,309 | 8/1972 | Harza ............................ 100/93 P X |
| 3,691,648 | 9/1972 | Kraus . |
| 3,785,281 | 1/1974 | Ligh . |
| 3,808,766 | 5/1974 | Hutchinson et al. . |
| 3,821,927 | 7/1974 | Stratman et al. . |
| 3,831,514 | 8/1974 | Jernstrom . |
| 3,861,117 | 1/1975 | DeFilippi . |
| 3,926,107 | 12/1975 | Dunlap et al. . |
| 4,004,398 | 1/1977 | Larsson et al. . |
| 4,374,491 | 2/1983 | Stortroen et al. . |
| 4,387,633 | 6/1983 | Ballantyne . |
| 4,455,931 | 6/1984 | Clifford et al. . |
| 4,552,720 | 11/1985 | Baker . |

OTHER PUBLICATIONS

Macek, Thomas J., *Biological Indicators, and the Effectiveness of Sterilization Procedures*, pp. 19–35.
U.S. Pharmacopeia XVIII, pp. 830–831.

Primary Examiner—Mark Rosenbaum
Attorney, Agent, or Firm—Kenyon & Kenyon

[57] ABSTRACT

The plastic syringe destruction device employs a cylinder and piston compaction unit together with heat to thermally smash plastic syringes into a compacted mass or slug. During compaction, the syringes are heated to temperatures between 100° C. and 200° C. to bring about melting of the syringes as well as sterilization. A removable transparent cover is also provided to permit only individual depositing of syringes into the cylinder when the main cover is in an opened position. A water injector nozzle is also provided as an option to permit compaction in a dry or wet state.

27 Claims, 5 Drawing Sheets

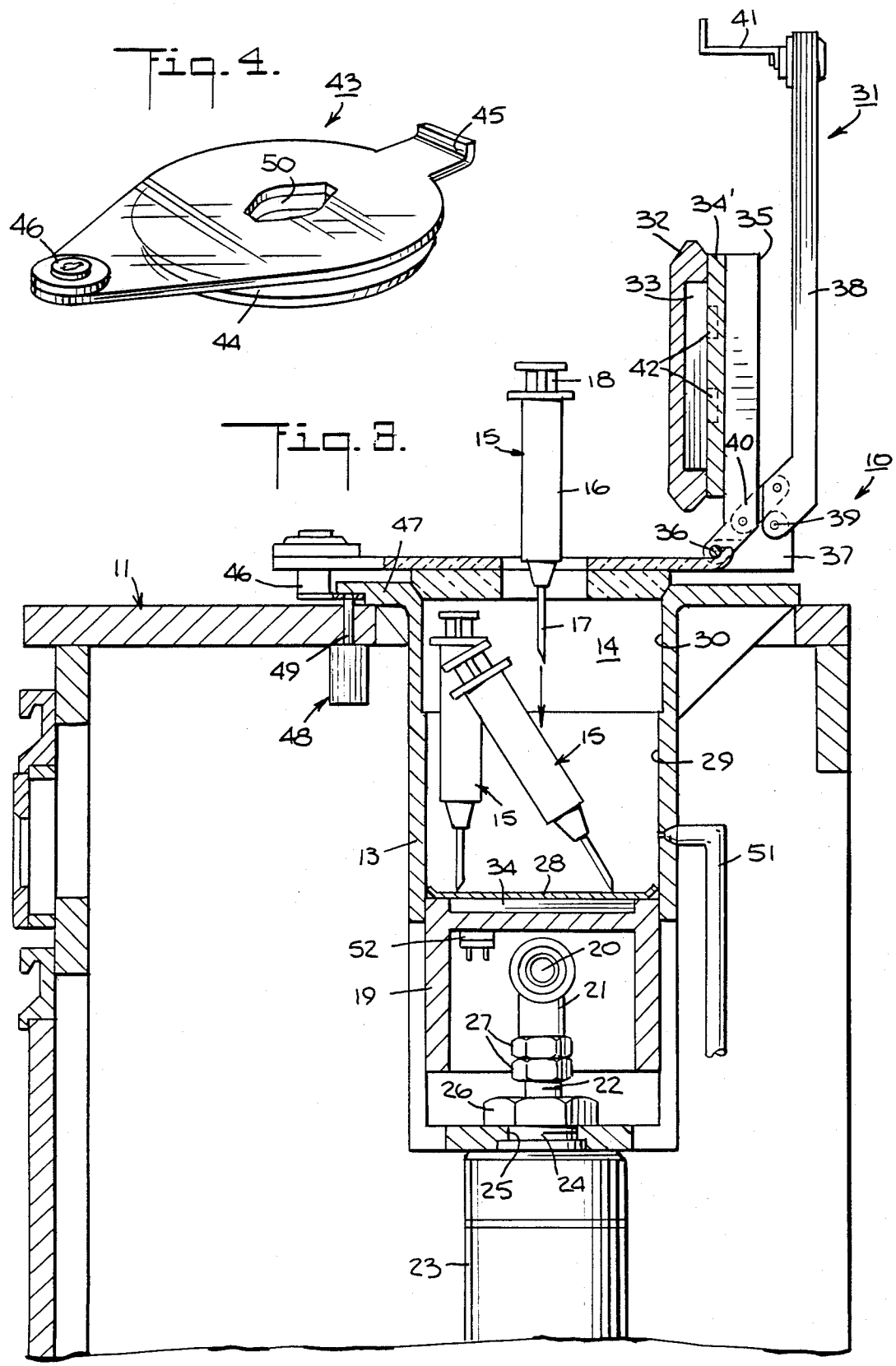

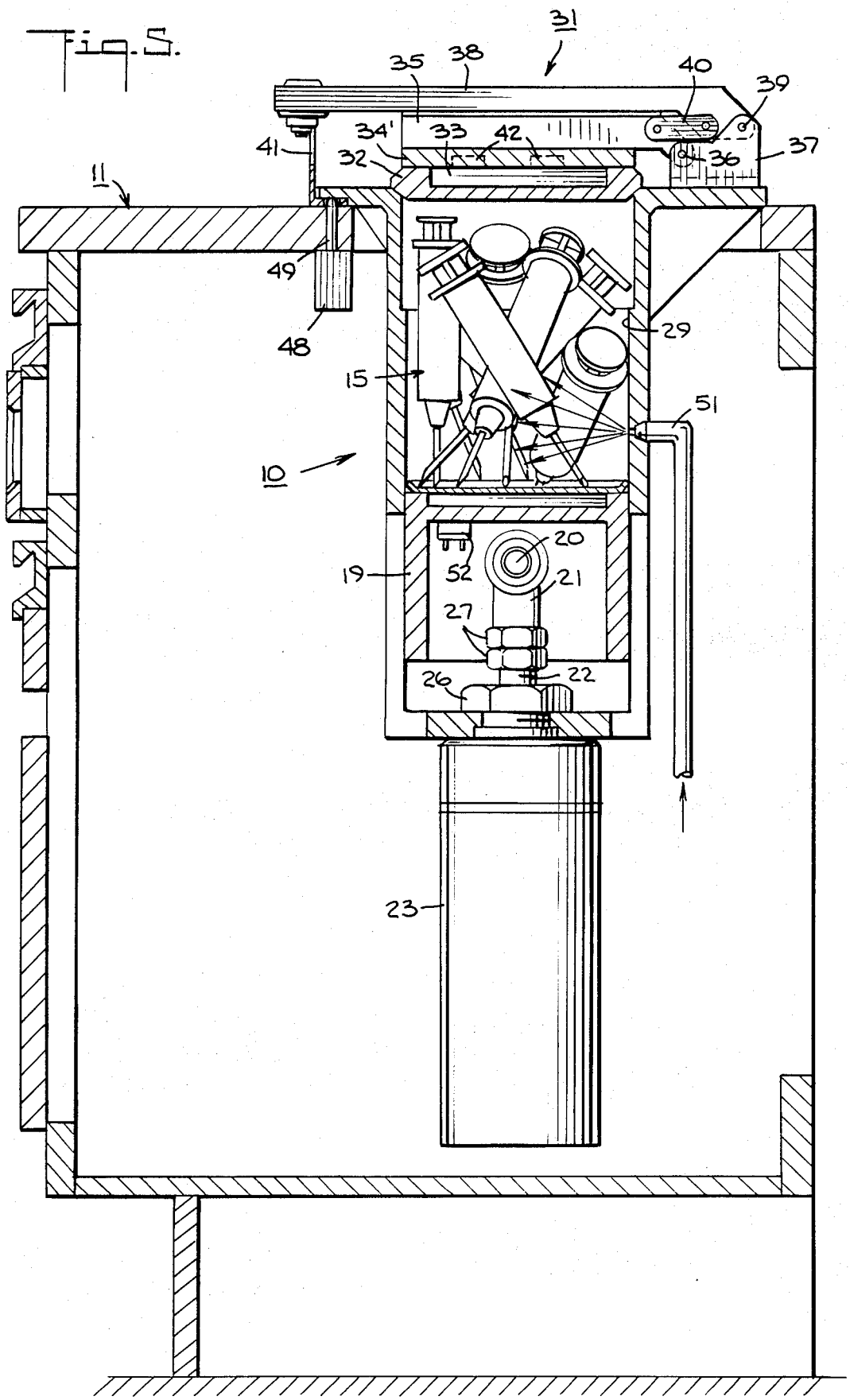

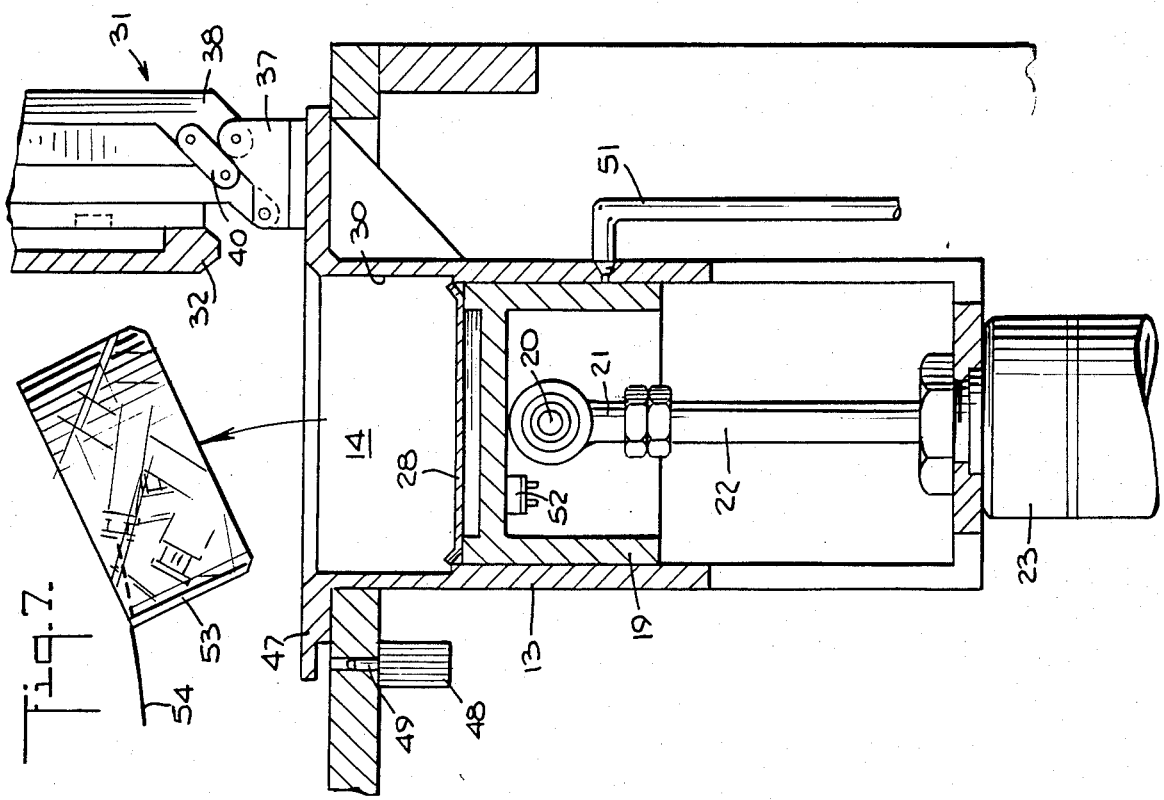
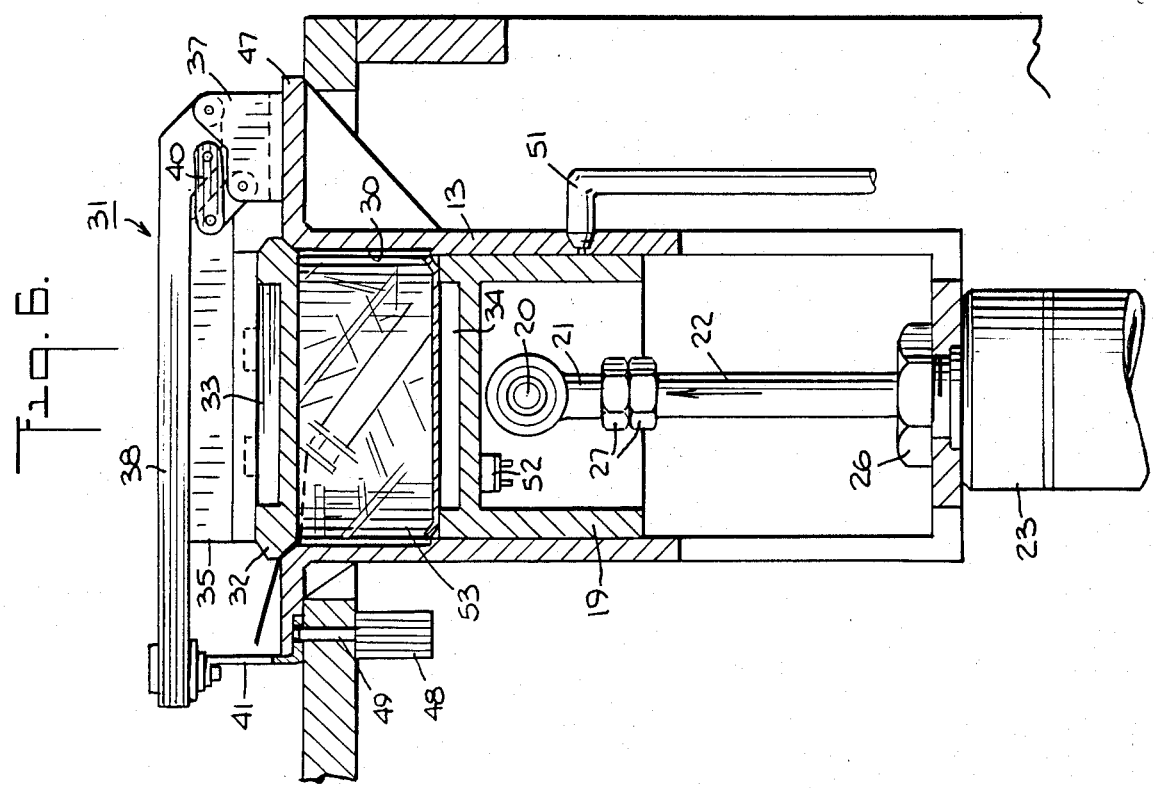

Fig. 8.
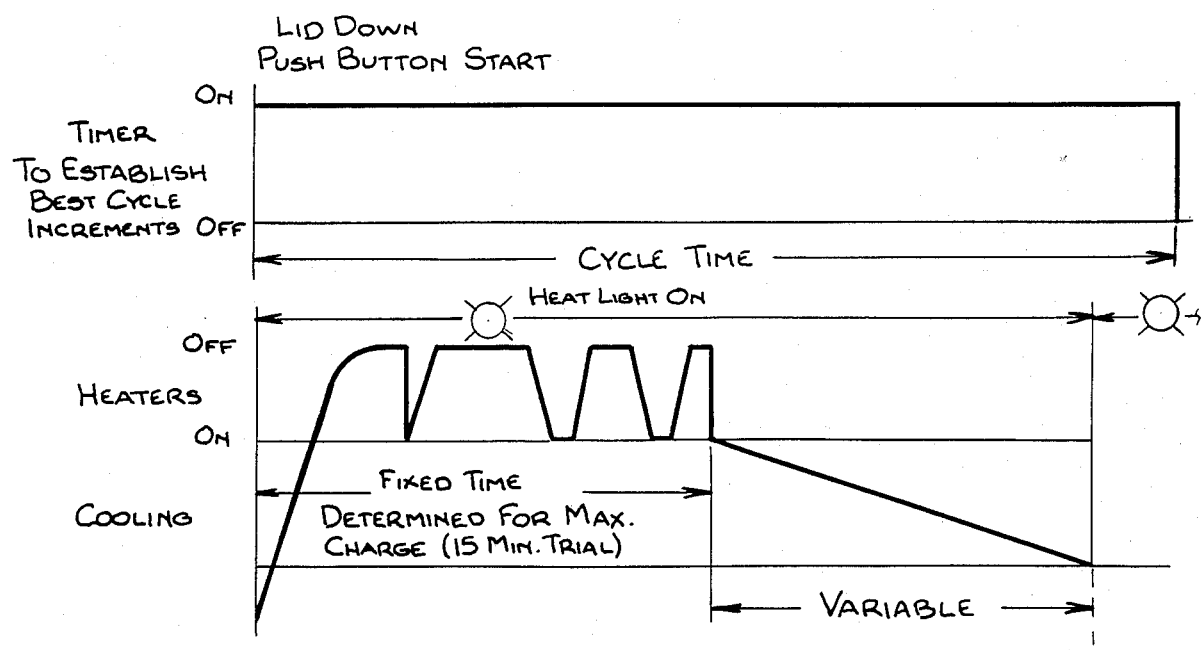
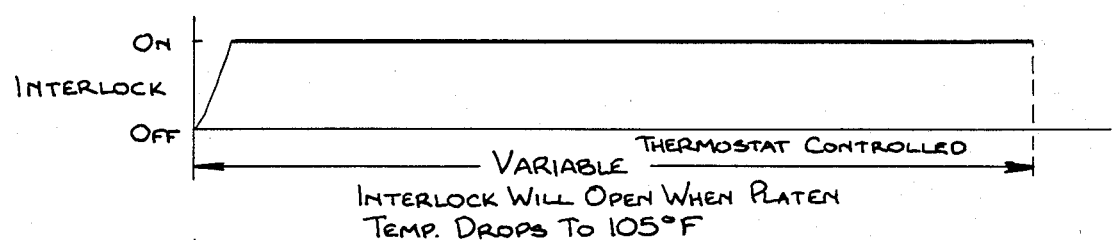
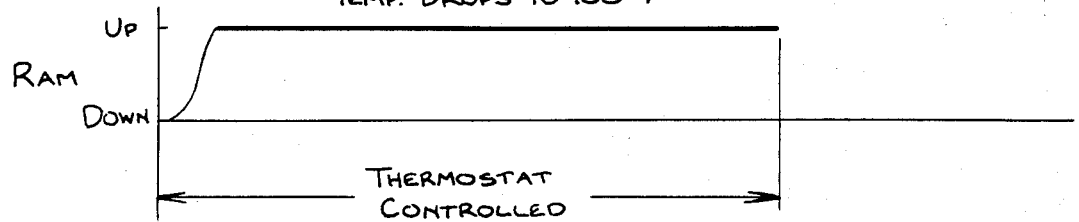
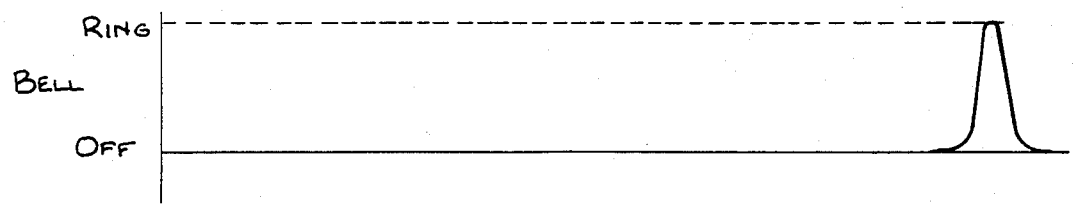

PLASTIC SYRINGE DESTRUCTION DEVICE

This invention relates to a plastic syringe destruction device.

As is known, various devices have been provided for the disposal of medical devices in either a hospital environment or an office environment. For example, U.S. Pat. No. 3,589,276 describes a destruction apparatus for hospitals which employs a grinding device in the form of disks for disintegrating articles fit through a tube into small particles. The apparatus also includes a compressing device formed of a cylinder and piston which serves to compact the ground particles and an electric heating device for heating the particles collected in the chamber to a temperature of about 200° C. to 300° C.

U S. Pat. No. 4,552,720 describes a debris compressing autoclave which employs steam for sterilization purposes as well as a compressing apparatus for compressing debris into a massive integral pellet for disposal. However, such a structure requires a liner of thermoplastic material to be disposed within the autoclave in order to form the pellet.

U.S. Pat. No. 2,731,208 describes an apparatus for disposing of contaminated waste which utilizes steam to sterilize the waste and a shredder to thereafter shred the sterilized material into a sewer.

U.S. Pat. No. 4,374,491 describes an apparatus which has one compartment in which waste may be sterilized by steam under pressure and then transferred into a second compartment for compaction by a ram.

Various other types of compactors for waste, some of which employ deodorizing chemicals which are sprayed into a compaction chamber, have also been known from U.S. Pat. Nos. 3,926,107; 3,831,514; 3,821,927; 3,808,766 and 3,785,281.

Still further have been known for shredding waste such as in U.S. Pat. No. 3,861,117 and for shredding, compressing and sterilizing refuse as described in U.S. Pat. No. 3,547,577.

However, the structures which have been known have been rather cumbersome and bulky. In addition, relatively large amounts of energy are required, for example, for shredding of waste.

It has also been known that plastic syringes which may have been contaminated and Which have sharp needles, require a great deal of care to ensure effective disposal. For example, since the syringes are made of plastic, simple compactor type disposal devices cannot readily compact the syringes into a small space. That is, the "memory" of the plastic tends to maintain the shape of the syringes even after being placed in a compactor. Further, because of the possibility of contamination, the syringes generally require very careful handling.

Accordingly, it is an object of the invention to provide a reliable low-cost device for the destruction of plastic syringes.

It is another object of the invention to provide for the destruction of plastic syringes with a minimal amount of handling.

It is another object of the invention to provide for the destruction and decontamination of plastic syringes in a simple manner.

It is another object of the invention to provide a syringe destruction device which can be of portable nature.

It is another object of the invention to be able to dispose of used syringes in a reliable and secure manner.

Briefly, the invention provides a plastic syringe destruction device which includes at least one cylinder mounted within a cabinet to define a chamber for receiving a plurality of used plastic syringes. In addition, the device employs a cover means which is movably mounted on the cabinet for movement between an open position providing access to the cylinder chamber and a closed position to close the chamber. In addition, the device includes a heating means for heating the syringes in the chamber to a temperature sufficient to permit melting of the syringes and a piston slidably mounted in the chamber for compacting the heated syringes in the chamber into a compacted mass.

The device is constructed so that the cabinet may have, for example, two piston and cylinder arrangements. In this case, one arrangement may be operated to compact a plurality of syringes while the other arrangement is inactive so as to be filled with used syringes while securing these syringes in a locked chamber.

In order to destroy the plastic syringes, the syringes are first placed in the cylinder chamber. Thereafter, the chamber is closed and the syringes are heated to a temperature sufficient to permit melting. Next, the heated syringes are compacted into a compacted mass which is a fraction of the original volume of the cylinder into which the syringes were placed. For example, the syringes may be compacted into a mass having a diameter in the range of 4.5 inches and thickness in the range of 0.75 inches. As such, the compacted mass or "slug" resembles a hockey puck.

After the compacted mass is cooled, the cover means is opened to permit removal of the compacted mass. To this end, a strip of heat resistant material may also be placed in the cylinder chamber prior to heating and compaction of the syringes. After compaction, the strip forms a handle to provide a means by which the compacted mass may be handled.

In order to facilitate removal of the compacted mass, the cylinder has a counter-bore at the open end opposite the piston for receiving the compacted mass. Thus, when the piston is withdrawn after compaction has been completed, the compacted mass remains at that end of the cylinder. Further, the cylinder may be provided with a plastic coating about the chamber to prevent sticking of the piston during compaction. The piston may also be provided with a wiper disk facing the chamber to sealingly engage the cylinder. Such a disk may be removed from time-to-time should the need arise due to wear.

The device may also be provided with a water injection nozzle which communicates with the cylinder chamber for injection of water into the chamber prior to heating of the syringes. The water injection serves to provide an atmosphere of less than 100% humidity. In this respect, the water facilitates compaction of the syringes.

The device may also include a removable transparent cover which can be selectively mounted over the cylinder chamber when the cover means is in an open position. This cover is also provided with a restricted opening of a size to permit passage of only a single syringe into the chamber. In this way, syringes may be deposited one at a time without opening and locking of the cover means. Further, this prevents drapes, swabs, sponges, catheters, guide wires, gloves and other refuse from being placed in the chamber.

Suitable catches are also provided on the cover means and the removable cover to provide for a secure locking arrangement.

These an other objects and advantages of the invention will become more apparent from the following detailed description taken in conjunction with the accompanying drawings wherein:

FIG. 3 illustrates a view taken on line III—III of FIG. 1;

FIG. 4 illustrates a perspective view of a removable cover in accordance with the invention;

FIG. 5 illustrates a view taken on line V—V of FIG. 2;

FIG. 6 illustrates a cross sectional view similar to FIG. 5 with the piston at the end of a compaction stroke;

FIG. 7 illustrates a view of the device during removable of a compacted mass; and FIG. 8 graphically illustrates the operation of a syringe destruction device in accordance with the invention.

Figure 1:
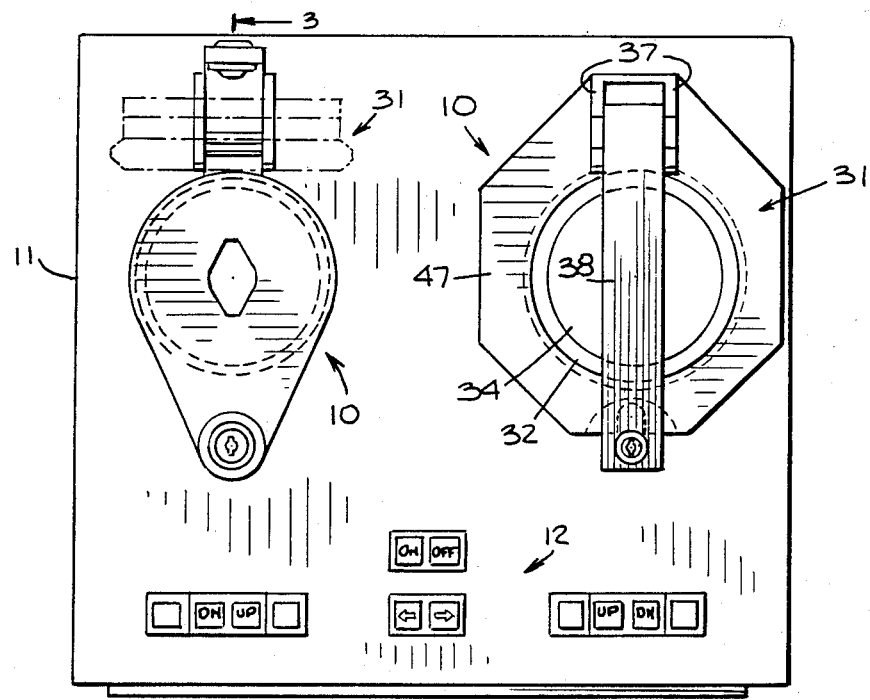
FIG. 1 illustrates a top view of a plastic syringe destruction device constructed in accordance with the invention.
Figure 2:
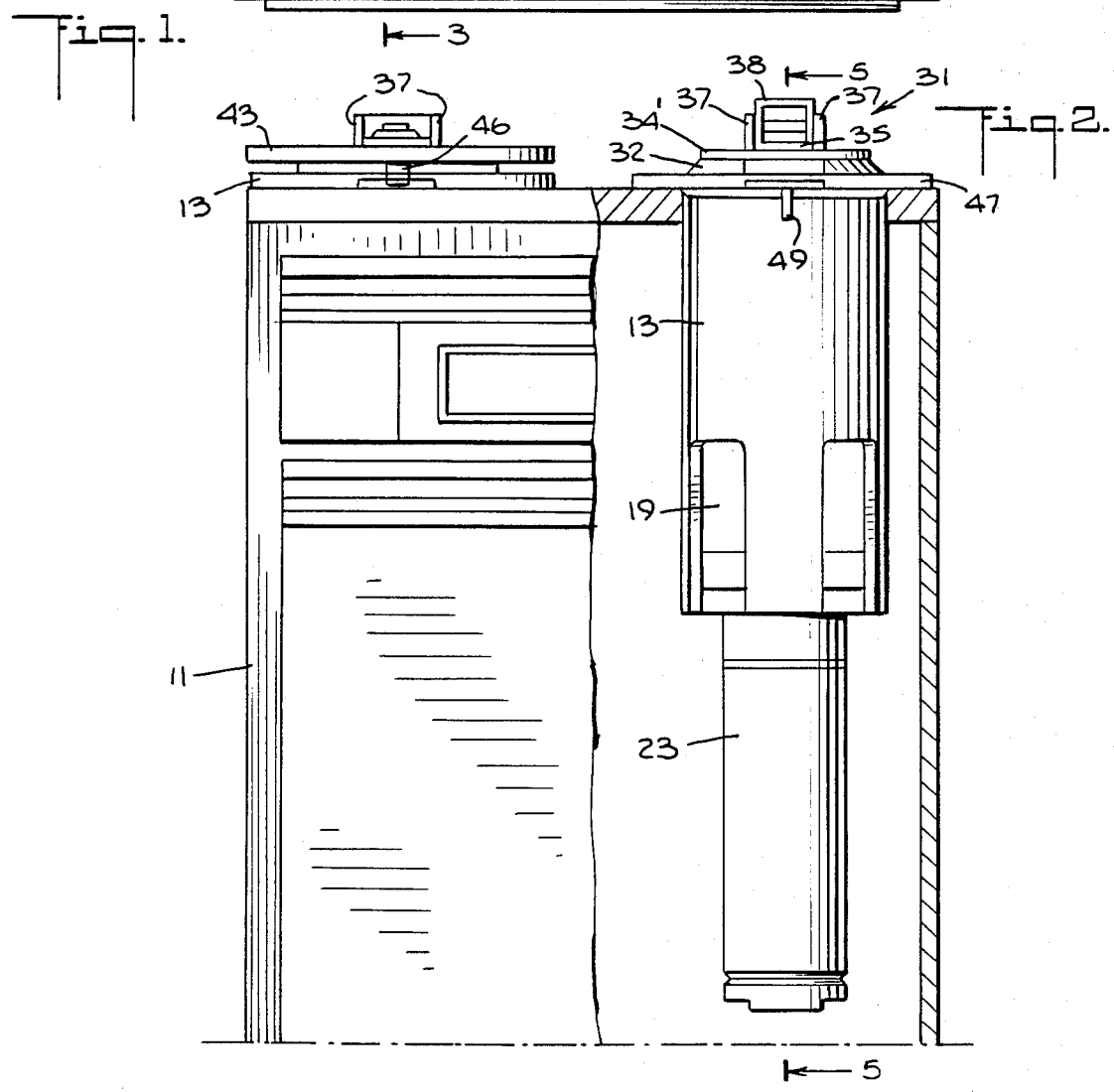
FIG. 2 illustrates a partial front cross-sectional view of the device of FIG. 1.

Referring to FIGS. 1 and 2, a pair of syringe destruction devices 10 are incorporated within a cabinet 11 which may be mounted in a fixed manner or which may be mounted on wheels or casters (not shown) so as to be portable. As indicated, the cabinet 11 is of generally box-like shape and may be made of any suitable materials. In addition, suitable controls are provided for operating each destruction device 10, for example in tandem manner. These controls are actuated by controls buttons 12 on the top surface of the cabinet 11.

Referring to FIG. 3, each device or compacting unit 10 is constructed in like manner. Thus, only one device 10 will be further described.

As indicated, each device 10 includes a cylinder 13 which defines a chamber 14 having an open upper end which is sized for receiving a plurality of used plastic syringes 15. In this respect, the syringes 15 may be of any conventional structure having, for example, a plastic housing 16 from which a metal needle 17 projects and a plunger 18 which is slidably mounted in the housing 16. The cylinder 13 also has a radial flange 47 which rests on the top of the cabinet 11 to support the cylinder 13 in depending relation.

In addition, a piston 19 is slidably mounted in the chamber 14, for example, at the lower end. The piston 19 is of hollow construction and is connected via a pin 20 and clevis 21 to a rod 22 which is reciprocally mounted within a pneumatic cylinder 23. Upon actuation of the cylinder 23, the rod 22 can be reciprocated along a vertical axis. In this respect, the pneumatic cylinder 23 has a threaded portion 24 through which the rod 22 passes and which passes through a bore 25 in the base of the cylinder 13 while a nut 26 is threaded onto the threaded portion 24 against the base of the cylinder 13 to secure the pneumatic cylinder 23 in place. A pair of lock nuts 27 are also provided for adjusting the clevis 21 on the rod 22 and, thus, the piston 19 relative to the pneumatic cylinder 23.

The piston 19 also carries a wiper disk 28, for example of a suitable non-stick material, which is slidably engaged v against the interior wall of the cylinder 13 as well as a heater disc 34.

The pneumatic cylinder 23 is connected to suitable controls so as to be actuated in a timed sequence.

The cylinder 13 and cover 19 are provided with a coating, for example, of a fluorocarbon and aluminum oxide material or the like so as to prevent sticking of the plastic of the syringes 15 to the walls of the cylinder 13. The interior of the cylinder 13 is also provided with a counterbore 30 or slight taper at the upper end. For example, where the chamber 14 has a diameter of 4.500 inches the counterbore 30 has a diameter of 4.510 inches.

Each destruction device 10 also includes a cover means 31 for selectively closing the open end of the cylinder chamber 14. In the position indicated in FIG. 3, the cover means 31 is in an open condition.

The cover means 31 includes a platen 32 which is sized to sealingly engage about the top end of the cylinder 13 to close off the chamber 14 (see FIG. 5) and which has a hard non-stick coating similar to that on the cylinder 13. In addition, the platen 32 houses a heater disk 33 of an electrically actuated type. This heater disk 33 cooperates with a similar heater disk 34 in the piston 19 to serve as a heating means for heating the chamber 14 in order to heat the syringes 15 therein to a temperature sufficient to permit melting of the syringes. An insulator 34' is disposed over the platen 32 and is secured along with the platen 32 to a carrier plate 35 which is pivotally mounted about a pin 36 secured within a pair of brackets 37 mounted on the top of the flange 47.

A cover plate 38 is also pivotally mounted via a pin 39 on the brackets 37 and is connected by a pair of toggle links 40 so as to pivot simultaneously therewith. The cover plate 38 carries a catch 41 at the distal end which is mounted in a rotatable manner. This catch 41 serves to secure the cover plate 38 in a closed position (see FIG. 3).

A pair of thermostats 42 are mounted in contiguous relation to the heater disk 33 and 34 and within the insulator 34' to generate signals indicating the heat generated within the cylinder chamber 14.

A removable transparent cover 43 is also provided for selective positioning over the open end of the chamber 14 when the cover means 31 is in the raised condition of FIG. 3. As indicated in FIGS. 3 and 4, the cover 43 has a circular portion 44 which is sized to fit within the opening of the cylinder 13. In addition, the cover has an upturned flange 45 at the proximal end which fits under the pivot pin 36 for the platen 32. In addition, a pivotally mounted catch 46 is provided at the distal end of the cover 43 for engaging under the radial flange 47 projecting from the cylinder 13. As indicated in FIG. 3, a lock in the form of a solenoid actuated lock 48 is mounted in the cabinet 11 beneath the flange 47. This lock 48 has a reciprocably mounted pin 49 which can be raised and lowered relative to the top surface of the cabinet 11 so as to abut against the flange 47 of the cylinder 13. When raised, the pin 49 fits within an aperture (not shown) in the catch 46 so as to lock the catch 46 in place and thus hold the cover 43 in place.

Referring to FIGS. 3 and 4, the cover 43 is provided with a restricted opening 50 which is sized to permit passage of only a single syringe 15 into the chamber 14. In this way, unwanted materials can be excluded from being placed in the chamber 14. In addition, by placing and locking the transparent cover 43 in place, there is no need for repeated opening and closing of the cover means 31 when depositing syringes in the cylinder 13.

Referring to FIG. 5, the solenoid lock 40 also serves to lock the rotatable catch 41 of the cover plate 38. In this respect, the catch 41 is pivotable about a vertical axis, as viewed, into a position under the flange 47 of the cylinder 13 while the pin 49 is movable into a slot or aperture (not shown) in the catch 41 to lock the same in place.

Referring to FIG. 3, each destruction device 10 is also provided with a water injection nozzle 51 which communicates with the chamber 14 near the lower end for the injection of water into the chamber 14. To this end, the nozzle 51 may be connected to a tank with a pump (not shown) so as to provide for portability of the destruction device 10 from place to place. Alternatively, for a fixed mounting, the delivery of water from a water main (not shown). As indicated, the nozzle 51 is disposed near the lower end of the cylinder chamber 14, that is, at a position slightly above the at rest or retracted position of the piston 19. The nozzle 51 serves to supply water into the chamber 14 prior to heating of the chamber so as to control the humidity within the chamber 14. In this respect, the injection of water provides an atmosphere of less than 100% humidity prior to heating.

The cabinet 11 may be provided with a suitable exhaust vent (not shown) for the venting of heated air from within the cabinet.

As shown in FIG. 3, a thermostat 52 is also provided within the piston 19 for sensing the heat within the chamber 14.

The pneumatic cylinder 23, solenoid lock 48, heater disks 33, 34, injection nozzle 51 and thermostats 42, 52 are all connected to the controls (not shown) so as to operate in programmed sequences.

Referring to FIG. 1, when in use, one device 10 is in the closed position as shown to the right of FIG. 1 in order to carry out a compacting operation while the other device 10 is in a deactivated position and disposed so as to receive syringes.

Referring to FIG. 3, in order to fill the cylinder 13, the transparent cover 43 is secured in place and syringes 15 can be passed through the opening 50 in the cover 43 from time-to-time until the cylinder 13 is filled.

In order to compact the syringes 15 within a filled cylinder 13, the transparent cover 43 is removed. To this end, the controls of the device 10 are actuated so that the pin 49 of the lock 48 is electronically retracted. The catch 46 can then be rotated away from the position underneath the flange 47 of the cylinder 13. Next, the cover can be lifted at the distal end so as to slide the upturned proximal end 45 from under the pin 36.

After removal of the cover 43, the cover means 31 is pivoted from the opened position to the closed position, as indicated in FIG. 5. At this time, the catch 41 is then rotated so as to pass under the flange 47 of the cylinder 13. The catch 41 is then locked in place by the pin 49 of the solenoid lock 40. For example, the controls of the device 10 may be actuated so as to move the pin 49 into the locking position or the pin 49 may be spring biased into the locking position as a normal position.

When the cover means 31 is in the closed position, the destruction device 10 is actuated so that water is injected via the nozzle 51, the heating disks 33, 34 activated to begin heating of the syringes 15 within the chamber 14 and the pneumatic cylinder 23 actuated so as to begin an upward stroke of the piston 19.

Since most of the plastics used for syringes are of the polypropylene and polyethylene type, the syringes 15 are heated to a range of from 100° C. to 200° C. and preferably in the range of from 135° C. to 150° C. These temperatures are sufficient to melt the plastic so as to destroy the memory of the plastic. That is, the plastic is remolded so as to be thermally "set" when in the plastic state. Of note, these temperatures are sufficient to provide for sterilization of the syringes 15 and are below the melting temperature of rubber stoppers.

Referring to FIG. 6, as the piston 19 moves upwardly within the cylinder 13 towards the secured platen 32, the syringes 15 begin to collapse and compress into a compacted mass. Upon completion of the stroke of the piston 19, the syringes 15 will be totally thermally smashed so that the compacted mass becomes set.

After cooling has occurred, the piston 19 is withdrawn in the downward direction. At this time, the compacted mass 53 remains at the upper end of the cylinder chamber 14 since the mass has been radially expanded in the counterbore 30. In this way, the counterbore 30 provides a stop to prevent the compacted mass 53 from moving downwardly with the piston 19. Since the compacted mass 53 will remain in place due to the counterbore 30, the piston 19 can be retracted away from the compacted mass 53 to enhance cooling of the compacted mass 53 by natural air convection.

Once the temperature within the cylinder 13 has decreased to a suitable extent, as determined by the thermostats 42, 52, the solenoid lock 40 will automatically release. At this time, the catch 41 can be rotated from under the flange 47 and the cover means 31 lifted into the opened position as indicated in FIG. 7. At this time, the compacted mass 53 which may be characterized as being in the form of a slug or hockey puck can be removed. To this end, the piston 19 can be actuated so as to move upwardly to expel the compacted mass 53 from the cylinder 13.

In order to facilitate handling of the compacted mass 53, a strip of heat resistant material may be placed in the cylinder 13 prior to closing of the cover means 31. Thus, upon compaction of the plastic syringes 15, the strip of material may provide a loop which functions as a handle 54 for the manual release or manual handling of the compacted mass 53.

The compacted mass 53 which is removed from a device 10 may be stored in a suitable drawer or compartment of the cabinet 11 until such time as a number of these compacted masses 53 can be boxed for disposal purposes. Thus, where the destruction device 10 is used, for example, in an office environment, the cabinet compartment may be emptied on a weekly basis whereas in a hospital environment, the compartment may be emptied on a daily or shift basis.

Referring to FIG. 1, the various indicators and buttons on the cabinet 11 indicate the state of operation of a selected device 10. For example, one pair of lighted buttons 54 may indicate whether the device 10 is "on" or "off". In addition, a pair of lighted buttons 55 adjacent the on/off buttons 54 may indicate by an arrow which device 10 is on. A similar pair of lights 56 may be used for each device 10 to indicate whether the piston therein is up or down. Another light 57 may indicate whether the heating means is on or off while a still further light 58 may indicate whether the solenoid lock is on or off.

The temperature, time and pressure parameters of the device 10 are adjustable to suit the needs of the user regarding the speed of processing. For example, as indicated in FIG. 8, a timer may be provided to establish the best cycle increments. In this respect, the timer would be connected so as to turn on only when the cover means 31 is in the closed position, i.e. when the heating disks 33, 34 of the heating means are in place. The timer may also be automatically reset when a cycle is interrupted so that a syringe charge within the cylinder 13 passes through a complete cycle.

The circuitry for the devices 10 is designed to prevent both from operating simultaneously. This allows one device 10 to act as a safe or bank for storage while the other is "cooking".

A cover interlock may also be provided to maintain the solenoid lock 40 in a locked condition when the temperature raises above, for example 110° F. (43° C.) and to de-energize when the temperature falls below this temperature. The indicator light 57 may also be lighted to show when the temperature is above this level.

Each pneumatic cylinder 23 may be operated by 4-way solenoid valves so as to move up and down (not shown). In addition, momentary rocker switches (not shown) may be provided to allow the piston 19 to rise without the cover means in the closed position for ejection of the compacted mass, if necessary, by by-passing the timer circuit. A sustained switch would prevent the piston 19 from retracting at the end of a timed cycle to keep heavy pressure on the cover means 31 if in an up position.

Once the cover means have been closed and locked, a momentary push button 54 can be depressed to start the cycle and the timer. The cycle may run, for example, for thirty minutes or until an indicator light goes out. The pneumatic cylinder solenoids are tied into a low temperature thermostat circuit for retraction for unloaded purposes at a low temperature. In this respect, the circuitry may be designed so that the piston moves up so long as this thermostat is closed, that is, after heat is applied.

The approximate relationships required to produce sterilized used plastic syringe compacted masses or "slugs" is as follows.

| Time (minutes) | Temperature (°F.) | Pressure (psig) |
| --- | --- | --- |
| 15 | 212 | 70 |
| 14 | 220 | 65 |
| 13 | 230 | 60 |
| 12 | 240 | 55 |
| 11 | 250 | 50 |
| 10 | 260 | 45 |
| 9 | 270 | 40 |
| 8 | 280 | 35 |
| 7 | 290 | 30 |
| 6 | 300 | 25 |
| 5 | 310 | 20 |

As indicated in FIG. 8, a suitable alarm in the form of a bell can be provided to indicate the end of a cycle.

The invention thus provides a plastic syringe destruction device of compact construction which can be operated with minimal energy to reliably and effectively thermally smash plastic syringes.

Further, the invention provides a relatively simple apparatus and method for destroying plastic syringes while at the same time sterilizing the syringes during destruction.

What is claimed is:

1. A plastic syringe destruction device comprising
   a cylinder defining a chamber having an open upper end for receiving a plurality of used plastic syringes;
   cover means for selectively closing said open end of said cylinder chamber;
   heating means including a heating disc for heating the syringes in said chamber to a temperature sufficient to permit remolding of the syringes; and
   a piston slidably mounted in said chamber for compacting the heated syringes in said chamber against said cover means under a pressure sufficient to remold the heated syringes into a set compacted mass.

2. A device as set forth in claim 1 wherein said cover means includes a movably mounted platen for disposition over said open end of said cylinder and a lock for securing said platen to said cylinder.

3. A device as set forth in claim 2 wherein said heating means includes an electrically operated heating disc in said platen and said piston.

4. A device as set forth in claim 1 wherein said cylinder has a counter bore at said upper end for receiving the compacted mass.

5. A device as set forth in claim 1 which further comprises a water injection nozzle communicating with a lower end of said chamber for injection of water into said chamber to regulate humidity therein.

6. A device as set forth in claim 1 which further comprises a removable transparent cover for selective positioning over said open end of said chamber, said cover having an opening of a size to permit passage of only a single syringe therethrough.

7. In combination
   a cabinet; and
   at least one destruction device including at least one cylinder mounted within said cabinet to define a chamber for receiving a plurality of used plastic syringes between an open position providing access to said chamber and a closed position to close said chamber, heating means including a heating disc for heating the syringes in said chamber to a temperature sufficient to permit remolding of the syringes, and a piston slidably mounted in said chamber under a pressure sufficient to remold the heated syringes into a set compacted mass.

8. The combination as set forth in claim 7 wherein said cylinder has a counter-bore at an end opposite said piston for receiving the compacted mass.

9. The combination as set forth in claim 7 wherein said cylinder has a non-stick coating about said chamber.

10. The combination as set forth in claim 7 wherein said piston includes a wiper disc facing said chamber and sealingly engaging said cylinder.

11. The combination as set forth in claim 7 which further comprises a water injection nozzle communicating with said chamber for injection of water into said chamber.

12. The combination as set forth in claim 7 wherein said cover means includes a platen for disposition over an open end of said chamber in opposition to said piston, a cover for holding said platen over said chamber and a catch for securing said cover in said closed position.

13. The combination as set forth in claim 12 which further comprises a lock on said cabinet for locking said catch in said closed position.

14. The combination as set forth in claim 13 wherein said cylinder has a radial flange at one end and said catch is pivotally mounted on said cover to engage under said flange.

15. The combination as set forth in claim 14 wherein said lock is a solenoid actuated lock mounted in said cabinet beneath said cylinder flange and having a pin for engaging said catch.

16. The combination as set forth in claim 12 wherein said heating means further includes a heating disc in said piston.

17. The combination as set forth in claim 7 which further comprises a removable transparent cover for selective mounting over said cylinder chamber, said cover having a restricted opening of a size to permit passage of only a single syringe into said chamber.

18. The combination as set forth in claim 17 wherein said cylinder has a radial flange at one end and said transparent cover includes a pivotally mounted catch for engaging under said flange.

19. The combination as set forth in claim 18 which further comprises a solenoid actuated lock mounted in said cabinet beneath said flange and having a pin for engaging said catch.

20. The combination as set forth in claim 19 wherein said cover means includes a platen for disposition over an open end of said chamber in opposition to said piston, a cover for holding said platen over said chamber and a catch for securing said cover in said closed position, said catch being pivotally mounted to engage under said flange and to engage with said pin.

21. The combination as set forth in claim 7 comprising a pair of said destruction devices in said cabinet to permit filling of one device while compacting syringes in the other device 22. A method of destructing plastic syringes comprising the steps of placing a plurality of plastic syringes in a chamber;

closing the chamber;

heating the syringes in the closed chamber to a temperature sufficient to permit remolding of the syringes; and compacting the heated syringes at a pressure sufficient to remold the syringes in a set compacted mass.

23. A method as set forth in claim 22 wherein the syringes are heated to a temperature of between 100° C. and 200° C.

24. A method as set forth in claim 22 which further comprises the step of injecting water into the chamber prior to heating of the syringes to provide an atmosphere of less than 100% humidity.

25. A method as set forth in claim 24 wherein the syringes are heated to a temperature of from 135° C. to 150° C.

26. A method as set forth in claim 22 wherein the compacted mass has a diameter in the range of 4.5 inches and a thickness in the range of 0.75 inches.

27. A method as set forth in claim 22 which further comprises the step of positioning a strip of heat resistant flexible material in said chamber prior to compaction of the syringes to provide the compacted mass with a handle for subsequent handling.

* * * * *

UNITED STATES PATENT AND TRADEMARK OFFICE
CERTIFICATE OF CORRECTION

PATENT NO. : 4,860,958

DATED : August 29, 1989

INVENTOR(S) : EMIL A. YERMAN

It is certified that error appears in the above-identified patent and that said Letters Patent is hereby corrected as shown below:

```
Column 1, line 37 after "further" insert -other structures-
Column 1, line 46 "Which" should be -which-
Column 3, line 35 "controls" should be -control- (2nd occurrence)
Column 3, line 67 delete "v"
Column 5, line 15 after "mounting," insert -the nozzle 51 may
    be connected to a suitable water line for-
Column 6, line 1 "rang ℗" should be -range-
Column 6, line 7 "ar e" should be -are-
```

Signed and Sealed this

Tenth Day of July, 1990

Attest:

HARRY F. MANBECK, JR.

*Attesting Officer*     Commissioner of Patents and Trademarks